(12) United States Patent
Slavtcheff et al.

(10) Patent No.: US 6,491,937 B1
(45) Date of Patent: Dec. 10, 2002

(54) CLEANSING WIPE ARTICLE AND METHOD OF MANUFACTURE

(75) Inventors: Craig Stephen Slavtcheff, Guilford, CT (US); Robert Edward Gott, Norwalk, CT (US); Alexander Paul Znaiden, Trumbull, CT (US); Filomena Augusta Macedo, Naugatuck, CT (US)

(73) Assignee: Unilever Home & Personal Care USA, Greenwich, CT (US)

( * ) Notice: Subject to any disclaimer, the term of this patent is extended or adjusted under 35 U.S.C. 154(b) by 0 days.

(21) Appl. No.: 09/915,429

(22) Filed: Jul. 26, 2001

Related U.S. Application Data

(60) Provisional application No. 60/262,486, filed on Jan. 17, 2001.

(51) Int. Cl.[7] .............................. A01N 25/34
(52) U.S. Cl. ..................... 424/402; 424/443
(58) Field of Search ................. 424/402, 443

(56) References Cited

U.S. PATENT DOCUMENTS

| | | | |
|---|---|---|---|
| 4,758,467 A | 7/1988 | Lempriere | 428/290 |
| 5,744,149 A | 4/1998 | Girardot | 424/402 |
| 5,863,663 A | 1/1999 | Mackey et al. | 428/486 |
| 5,951,991 A | 9/1999 | Wagner et al. | 424/407 |
| 5,952,043 A | 9/1999 | Mackey et al. | 427/209 |
| 5,972,361 A | 10/1999 | Fowler et al. | 424/402 |
| 5,980,931 A | 11/1999 | Fowler et al. | 424/443 |
| 6,074,655 A | 6/2000 | Fowler et al. | 424/402 |
| 6,132,746 A | * 10/2000 | Hasenoehrl et al. | 424/402 |
| 6,153,208 A | 11/2000 | McAtee et al. | 424/402 |

FOREIGN PATENT DOCUMENTS

| | | |
|---|---|---|
| WO | 01/08655 | 2/2001 |
| WO | 01/08656 | 2/2001 |
| WO | 01/08657 | 2/2001 |
| WO | 01/08658 | 2/2001 |

OTHER PUBLICATIONS

International Search Report.

* cited by examiner

*Primary Examiner*—Michael G. Hartley
*Assistant Examiner*—Konata M. George
(74) *Attorney, Agent, or Firm*—Milton L. Honig

(57) ABSTRACT

A disposable substantially dry foamable product is described including a water-insoluble substrate such as a flexible web, the substrate having first and second major surfaces, with a plurality of moguls spaced apart on the first major surface and a foamable composition deposited in major amounts on the second surface and a minor amount on the first surface. A method for producing the product is also described which employs the moguls in juxtaposition to a guide roller to establish space between a surface of the roller and the first surface of the substrate. Foamed composition is deposited onto the second surface which by seepage through apertures in the substrate allow a minor portion of the coating composition to deposit on the first surface of the substrate.

11 Claims, 2 Drawing Sheets

CLEANSING WIPE ARTICLE AND METHOD OF MANUFACTURE

This application claims the benefit of U.S. Provisional Application No. 60/262,486 filed Jan. 17, 2001.

BACKGROUND OF THE INVENTION

1. Field of the Invention

The invention relates to a substantially dry, disposable foamable wipe article with physical features allowing for improved manufacture. The article is especially useful for personal cleansing and conditioning of skin or hair.

2. The Related Art

Traditional personal cleansing vehicles have been in the form of gels, bars and pourable liquid products. These forms are highly effective for cleansing purposes. Nevertheless, they are somewhat boring and, indeed, have some deficiencies. Often consumers combine the cleaning chemicals delivered by gels, bars and liquids with a wash cloth. Advantages of a cloth include improved spreadability, abrasive action and a pleasant ergonomic handfeel. Realization of such advantages for combining cleansing chemicals with a wipe have led to a rather large body of technology.

Among the most recent additions are a series of disclosures concerning substantially dry, disposable personal cleansing products activated upon use by wetting. Illustrative is U.S. Pat. No. 5,972,361 (Fowler et al.) disclosing a disposable, single use personal care cleansing and conditioning product wherein a lathering surfactant and oil soluble conditioning agent are during manufacture each separately applied to a substrate. Similar disclosures are found in U.S. Pat. No. 6,074,655 (Fowler et al.), U.S. Pat. No. 5,951,991 (Wagner et al.) and U.S. Pat. No. 6,132,746 (Hasenoehrl et al.).

U.S. Pat. No. 5,952,043 and U.S. Pat. No. 5,863,663, both to Mackey et al., describe typical procedures for manufacture of dry wipes. Application of the chemicals to the substrate is reported to be either through spraying, rotogravure coating or by screen printing. Coatings are simply applied to either or both surfaces of the substrate. FIG. 2 describes a system where the substrate passes between a pair of presses thereby simultaneously coating each surface of the substrate. Amounts of transferred surfactant or conditioning emulsion is reported to be controlled by either of two general adjustments. One of these is by control of the width of the nip area between the contact cylinders or other nip areas of the presses. The second general manner of adjustments is achieved through a change in the relief (valley depth) or print pattern on the areas of the cylinders contacting the substrate.

Among problems associated with the process is selectivity of deposition, especially where different amounts and patterns of chemicals must be deposited on opposite sides of the substrate web. In particular, it may be desirable to produce a wipe where one surface bears a major amount of cleansing chemicals and the opposite surface is limited to a much smaller amount, but the latter being deposited in defined areas. Articles of this type have the advantage that, with the aid of cues, the consumer will wet the chemically heavier deposited side and obtain instantly a richer foam. On the other hand, for those consumers who have missed the cue, there still will be a small amount of foam generated on the side not intended for cleansing.

Accordingly, it is an object of the present invention to provide a disposable, substantially dry cleansing product which includes a wiping substrate and a foamable composition wherein a major portion of the composition is applied onto one side of the wiping substrate and a minor portion on the other.

Another object of the present invention is to provide a disposable, substantially dry cleansing product formed as flexible wiping cloth, with one surface of the wiping cloth having a different surface topography and a different amount of composition deposited thereon than an opposite second surface.

Still another object of the present invention is to provide a method for producing a disposable, substantially dry cleansing product in a process which readily allows coating of juxtaposed opposite surfaces of a wiping substrate but requiring application of the foamable composition to only a first of those surfaces.

SUMMARY OF THE INVENTION

A substantially dry cleansing product is provided which includes:

(i) a water insoluble substrate defined by juxtaposed first and second major surfaces, the first major surface being formed with a plurality of upwardly projecting moguls spaced apart from one another; and (ii) a foamable composition including a lathering surfactant wherein more of the composition is deposited on the second major surface than on the first major surface of the substrate Also provided is a method for producing a cleansing article which includes an apertured water-insoluble substrate having first and second major surfaces opposite one another, the first major surface being formed with a plurality of spaced apart moguls, and the article delivering a foamable composition including a lathering surfactant, the method including:

feeding the substrate onto a guide roller, the first major surface of the substrate being juxtaposed against a surface of the guide roller;

applying the foamable composition to the second major surface of the substrate while the first major surface remains juxtaposed against the guide roller; and allowing a minor amount of the applied foamable composition to transfer through the apertured substrate from the second to the first major surface.

BRIEF DESCRIPTION OF THE DRAWING

Further objects, advantages and features of the present invention will become more readily apparent from consideration of the following drawing in which.

DETAILED DESCRIPTION OF THE INVENTION

Now it has been found that providing a pattern of raised moguls onto a first surface of a substrate aids in achieving partial coating of that surface when an opposite surface is supplied with a foamable composition. The moguls function as spacers between the first surface of the substrate and a surface of the guide roller. Foamable composition when applied to the opposite surface of the substrate can penetrate through apertures in the substrate and, as a result of the spaced apart relationship seep through to the first surface of the substrate between the moguls. Without the moguls, pressure of guide roller against coating roller would reduce the interstitial space into which seepage to the first surface occurs.

Figure 1:
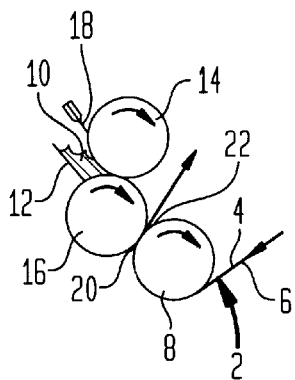
FIG. 1 is a first embodiment of a coating method utilizing a three roll nip.

FIG. 1 illustrates a typical manufacture embodiment of the present invention. A substrate 2 with first and second surfaces 4, 6 is fed to a guide roller 8 rotating in a clockwise direction. A foamable composition 10 is held within a dam 12 adjacent a pair of coating rollers 14, 16 both of which rotate in a clockwise direction. A doctor blade 18 ensures an even spread of the composition on the coating rollers. The composition 10 is deposited through contact of roller 16 against second surface 6 of the substrate at the nip 20 between coating roller 16 and guide roller 8. Pressure between these rollers causes composition deposited onto substrate surface 2 to seep through apertures in the substrate and to a small extent spread onto the second surface 4 in areas between the moguls. Improved seepage and spreading is possible because the moguls offset surface 4 from the guide roller surface 22 in the nip 20. By this procedure, a major amount of the composition can be deposited on one surface of the substrate while simultaneously depositing a minor amount on a second surface of the substrate.

Advantageously the amount of foamable composition deposited onto the second surface may range from more than 50 to 99.9%, preferably from about 60 to about 98%, more preferably from about 85 to about 95% by weight. Deposition on the first surface may range from about 0.01 to less than 50%, preferably from about 0.1 to about 30%, optimally from about 1 to about 15% by weight of total foamable composition deposited onto the substrate. Advantageously the ratio of deposited foamable composition present on the first and second surfaces may range from about 1:1,000 to about 2:3, preferably from about 1:100 to about 1:2, optimally from about 1:20 to about 1:10 by weight.

Figure 2:
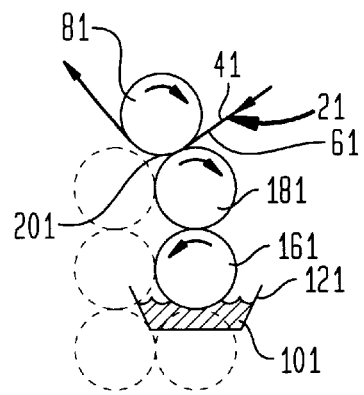
FIG. 2 is a second embodiment of a coating method employing a three roll differential.

FIG. 2 illustrates a second coating method employing a three roll reversed differential. Substrate 21 having a first surface 41 dotted with moguls and an opposite surface 61 is fed to a guide roller 81. Foamable composition 101 is held in a reservoir 121. A counter clockwise rotating coating roll 161 delivers a film of composition 101 to a clockwise rotating coating roll 181. Deposition of composition 101 onto the substrate surface 61 occurs at nip 201 where coating roller 181 contacts the substrate 21 and presses against guide roller 81. Moguls on surface 41 of the substrate function as spacers between surface 41 and the guide roller 81. Seepage of composition 101 through apertures in the substrate is thereby facilitated and some of the composition deposits between the moguls on the surface of the web facing the guide roller.

Figure 3:
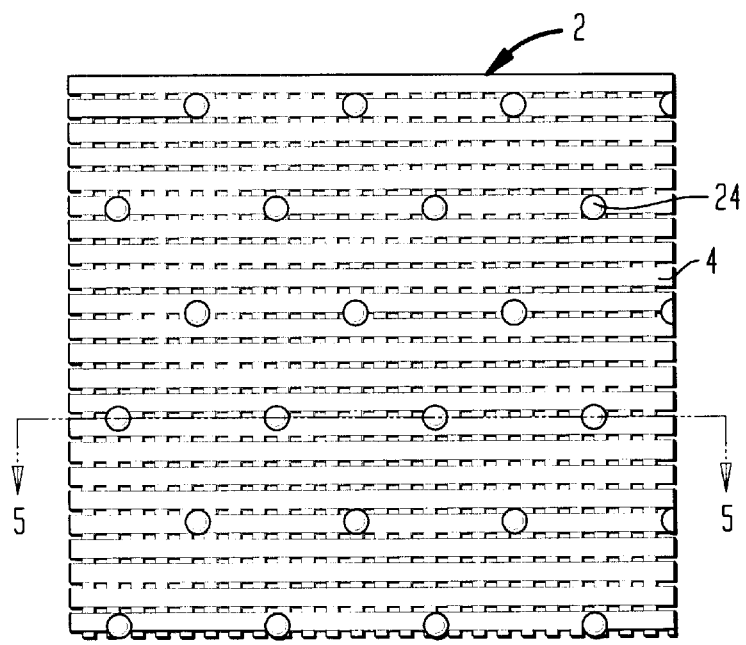
FIG. 3 is a top plan view of a substrate patterned with conical shaped moguls dotting a first surface thereof.
Figure 5:
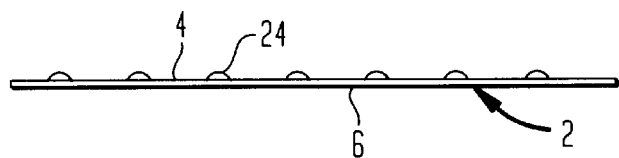
FIG. 5 is a cross-sectional view of the substrate taken along line 5—5 of FIG. 3.

FIG. 3 illustrates a typical regular pattern of moguls 24 as a pattern of raised dots projecting from surface 4. The moguls are best viewed in FIG. 5 where in cross section the moguls are shown as approximately rounded, raised projections.

Figure 4:
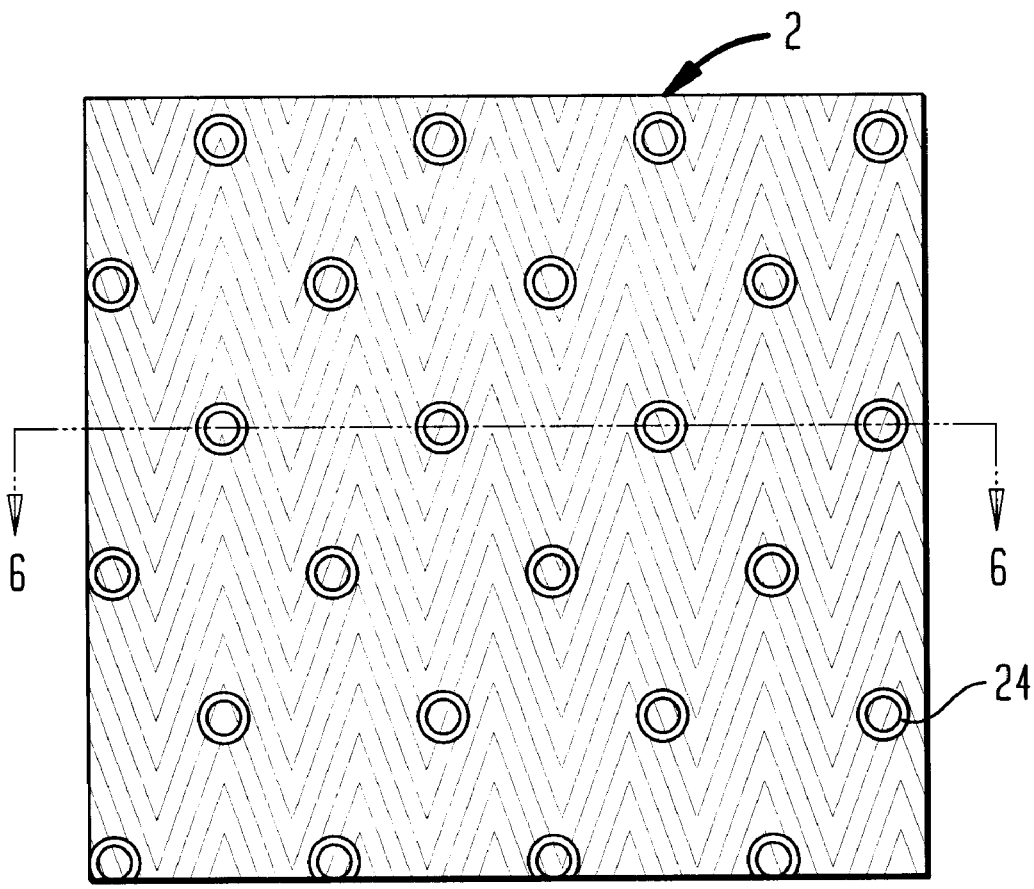
FIG. 4 is a top plan view of the second embodiment of a substrate with donut shaped moguls arranged along a first surface of the substrate.
Figure 6:
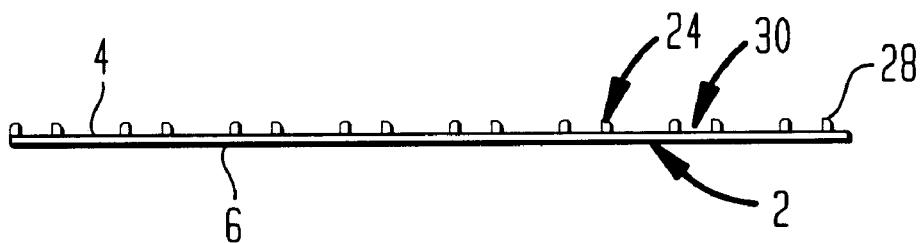
FIG. 6 is a cross-sectional view of the substrate taken along line 6—6 of FIG. 4.

FIG. 4 illustrates a second embodiment of the moguls showing them in donut configuration. The cross-sectional view of FIG. 6 illustrates the donut shape of mogul 24 having a rim 28 and a caldera 30 defining an area of no mogul material deposition.

Shapes other than conical or donut ones may be useful. Shapes may be fanciful or descriptive. Among the descriptive shapes may be letters of the alphabet or alphanumerics or combinations thereof.

Fanciful shapes includes stars, squares, polygons, triangles and irregular patterns. Not all moguls need be the same. Neither is it necessary to have moguls in a regular pattern, although regularity is preferred. Particularly preferred is where the moguls are separated from one another at their center by a distance of about 0.2 to about 4 cm, preferably from about 0.5 to about 3 cm, optimally from about 1 to about 2 cm. Substrates of this invention will advantageously have apertures at regular intervals which may range from about 0.1 mm to about 5 mm, preferably from about 1 to about 3 mm, optimally from about 1 to about 2 mm in any dimensional direction.

Where the moguls are donuts, it is particularly advantageous to locate at least some of the apertures in the caldera 30. Donuts are preferred over conical outwardly tapered structures (e.g. cones). The latter often are abraded losing their tips when consumers during cleansing use towelettes with those structures. Broken-off tips represent an aesthetically displeasing result.

Many other types of coating methods can be suitable in addition to those two embodiments described. For instance gravure, flexo and slot die procedures are available.

Subsequent to coating, the resultant substrates may be dried in an oven, cut to appropriate size, folded and packaged.

Substrates prior to the coating process will be provided with a mogul array. In one embodiment, the moguls will be of a material different from that of the web forming the substrate. Materials particularly preferred for the moguls are synthetic polymers, particularly elastomers such as those formed as homo and copolymers of monomers selected from the group consisting of styrene, butadiene, acrylonitrile, vinyl acetate, vinyl chloride, vinylidene chloride, vinyl pyridine, acrylamide, $C_2$–$C_8$ unsaturated mono- or di- carboxylic acid or ester thereof (e.g. maleic anhydride, acrylic acid, methacylic acid, ethyl acrylate, ethyl methacrylate), isoprene, divinyl benzene and combinations thereof. The elastomers often are deposited onto the web as an aqueous latex with a drying procedure depositing the mogul. Substrates with moguls are commercially available from Freudenberg Industries.

An essential element of compositions according to the present invention is that of a lathering surfactant. By a "lathering surfactant" is meant a surfactant, which when combined with water and mechanically agitated generates a foam or lather. Preferably, these lathering surfactants should be mild, which means that they must provide sufficient cleansing or detersive benefits but not overly dry the skin or hair, and yet meet the lathering criteria described above.

The products of the present invention typically comprise a lathering surfactant in an amount from about 0.5% to about 40%, preferably from about 0.75% to about 20%, and more preferably from about 1% to about 10%, based on the weight of the foamable composition.

A wide variety of lathering surfactants are useful herein and include those selected from the group consisting of anionic, nonionic, cationic, amphoteric and lathering surfactant mixtures thereof.

Among the anionic lathering surfactants useful herein are the following non-limiting examples which include the classes of:

(1) Alkyl benzene sulfonates in which the alkyl group contains from 9 to 15 carbon atoms, preferably 11 to 14 carbon atoms in straight chain or branched chain configuration. Especially preferred is a linear alkyl benzene sulfonate containing about 12 carbon atoms in the alkyl chain.

(2) Alkyl sulfates obtained by sulfating an alcohol having 8 to 22 carbon atoms, preferably 12 to 16 carbon atoms. The alkyl sulfates have the formula $ROSO_3{-}M^+$ where R is the $C_{8-22}$ alkyl group and M is a mono- and/or divalent cation.

(3) Paraffin sulfonates having 8 to 22 carbon atoms, preferably 12 to 16 carbon atoms, in the alkyl moiety. These surfactants are commercially available as Hostapur SAS from Hoechst Celanese.

(4) Olefin sulfonates having 8 to 22 carbon atoms, preferably 12 to 16 carbon atoms. Most preferred is sodium $C_{14}$–$C_{16}$ olefin sulfonate, available as Bioterge AS 40®

(5) Alkyl ether sulfates derived from an alcohol having 8 to 22 carbon atoms, preferably 12 to 16 carbon atoms, ethoxylated with less than 30, preferably less than 12, moles of ethylene oxide. Most preferred is sodium lauryl ether sulfate formed from 2 moles average ethoxylation, commercially available as Standopol ES-2®

(6) Alkyl glyceryl ether sulfonates having 8 to 22 carbon atoms, preferably 12 to 16 carbon atoms, in the alkyl moiety.

(7) Fatty acid ester sulfonates of the formula: $R^1CH(SO_3{-}M+)CO_2R^2$ where $R^1$ is straight or branched alkyl from about $C_8$ to $C_{18}$, preferably $C_{12}$ to $C_{16}$, and $R^2$ is straight or branched alkyl from about $C_1$ to $C_6$, preferably primarily $C_1$, and M+ represents a mono- or divalent cation.

(8) Secondary alcohol sulfates having 6 to 18, preferably 8 to 16 carbon atoms.

(9) Fatty acyl isethionates having from 10 to 22 carbon atoms, with sodium cocoyl isethionate being preferred.

(10) Dialkyl sulfosuccinates wherein the alkyl groups range from 3 to 20 carbon atoms each.

(11) Alkanoyl sarcosinates corresponding to the formula $RCON(CH_3)CH_2CH_2CO_2M$ wherein R is alkyl or alkenyl of about 10 to about 20 carbon atoms and M is a water-soluble cation such as ammonium, sodium, potassium and trialkanolammonium. Most preferred is sodium lauroyl sarcosinate.

(12) Alkyl lactylates wherein the alkyl groups range from 8 to 12 carbon atoms, with sodium lauroyl lactylate sold as Pationic 138 C® available from the Patterson Chemical Company as the most preferred.

(13) Taurates having from 8 to 16 carbon atoms, with cocoyl methyl taurate being preferred.

Nonionic lathering surfactants suitable for the present invention include $C_{10}$–$C_{20}$ fatty alcohol or acid hydrophobes condensed with from 2 to 100 moles of ethylene oxide or propylene oxide per mole of hydrophobe; $C_2$–$C_{10}$ alkyl phenols condensed with from 2 to 20 moles of alkylene oxides; mono- and di-fatty acid esters of ethylene glycol such as ethylene glycol distearate; fatty acid monoglycerides; sorbitan mono- and di-$C_8$–$C_{20}$ fatty acids; and polyoxyethylene sorbitan available as Polysorbate 80 and Tween 80® as well as combinations of any of the above surfactants.

Other useful nonionic surfactants include alkyl polyglycosides, saccharide fatty amides (e.g. methyl gluconamides) as well as long chain tertiary amine oxides. Examples of the latter category are:

dimethylododecylamine oxide, oleyldi(2-hydroxyethyl) amine oxide, dimethyloctylamine oxide, dimethyidecylamine oxide, dimethyltetradecylamine oxide, di(2-hydroxyethyl)tetradecylamine oxide, 3-didodecyloxy-2-hydroxypropyidi(3-hydroxypropyl)amine oxide, and dimethylhexadecylamine oxide.

Amphoteric lathering surfactants useful for the present invention include aliphatic secondary and tertiary amines, preferably wherein the nitrogen is in a cationic state, in which the aliphatic radicals can be straight or branched chain and wherein one of the radicals contains an ionizable water solubilizing group such as carboxy, sulphonate, sulphate, phosphate or phosphonate. Illustrative substances are cocamidopropyl betaine, cocamphoacetate, cocamphodiacetate, cocamphopropionate, cocamphodipropionate, cocamidopropyl hydroxysultaine, cetyl dimethyl betaine, cocamidopropyl PG-dimonium chloride phosphate, coco dimethyl carboxymethyl betaine, cetyl dimethyl betaine and combinations thereof.

A necessary element of the present invention is that of a water insoluble substrate. By "water insoluble" is meant the substrate does not dissolve or readily break apart upon immersion in water. A wide variety of materials can be used as the substrate. The following non-limiting characteristics are desirable: (i) sufficient wet strength for use, (ii) sufficient abrasivity, (iii) sufficient loft and porosity, (iv) sufficient thickness, and (v) appropriate size.

Non-limiting examples of suitable insoluble substrates which meet the above criteria include non-woven substrates, woven substrates, hydro-entangled substrates, air entangled substrates and the like.

Preferred embodiments employ non-woven substrates since they are economical and readily available in a variety of materials. By non-woven is meant that the layer is comprised of fibers which are not woven into a fabric but rather are formed into a sheet, particularly a tissue. The fibers can either be random (i.e., randomly aligned) or they can be carded (i.e. combed to be oriented in primarily one direction). Furthermore, the non-woven substrate can be composed of a combination of layers of random and carded fibers.

Non-woven substrates may be comprised of a variety of materials both natural and synthetic. By natural is meant that the materials are derived from plants, animals, insects or byproducts. By synthetic is meant that the materials are obtained primarily from various man-made materials or from material that is usually a fibrous web comprising any of the common synthetic or natural textile-length fibers, or mixtures thereof.

Non-limiting examples of natural materials useful in the present invention are silk fibers, keratin fibers and cellulosic fibers. Non-limiting examples of keratin fibers include those selected from the group consisting of wool fibers, camel hair fibers, and the like. Non-limiting examples of cellulosic fibers include those selected from the group consisting of wood pulp fibers, cotton fibers, hemp fibers, jute fibers, flax fibers, and mixtures thereof. Wood pulp fibers are preferred while all cotton fibers (e.g. cotton pads) are normally avoided.

Non-limiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers and mixtures thereof. Examples of some of these synthetic materials include acrylics such as Acrilan®, Creslan®, and the acrylonitrile-based fiber, Orlon®; cellulose ester fibers such as cellulose acetate, Amel®, and Acele®; polyamides such as Nylons (e.g., Nylon 6, Nylon 66, Nylon 610 and the like; polyesters such as Fortrel®, Kodel®, and the polyethylene terephthalate fibers, Dacron®; polyolefins such as polypropylene, polyethylene; polyvinyl acetate fibers and mixtures thereof.

Non-woven substrates made from natural materials consist of webs or sheets most commonly formed on a fine wire screen from a liquid suspension of the fibers.

Substrates made from natural materials useful in the present invention can be obtained from a wide variety of commercial sources. Non-limiting examples of suitable commercially available paper layers useful herein include Airtex®, an embossed airlaid cellulosic layer having a base weight of about 71 gsy, available from James River Corporation, Green Bay, Wis.; and Walkisoft®, an embossed airlaid cellulosic having a base weight of about 75 gsy, available from Walkisoft U.S.A., Mount Holly, N.C.

Non-woven substrates made from synthetic material useful in the present invention can also be obtained from a wide variety of commercial sources. Non-limiting examples of suitable non-woven layer materials useful herein include HFE-40-047, an apertured hydroentangled material containing about 50% rayon and 50% polyester, and having a basis weight of about 43 grams per square yard (gsy), available from Vertec, Inc., Walpole, Mass.; HEF 140-102, an apertured hydro-entangled material containing about 50% rayon and 50% polyester, and having a basis weight of about 56 gsy, available from Veratec, Inc., Walpole, Mass.; Novenet® 149-191, a thermno-bonded grid patterned material containing about 69% rayon, about 25% polypropylene, and about 6% cotton, and having a basis weight of about 100 gsy, available from Veratec, Inc., Walpole, Mass.; HEF Nubtex® (149-801, a nubbed, apertured hydro-entangled material, containing about 100% polyester, and having a basis weight of about 70 gsy, available from Veratec, Inc. Walpole, Mass.; Keybak® 951V, a dry formed apertured material, containing about 75% rayon, about 25% acrylic fibers, and having a basis weight of about 43 gsy, available from Chicopee Corporation, New Brunswick, N.J.; Keybak® 1368, an apertured material, containing about 75% rayon, about 5% polyester, and having a basis weight of about 39 gsy, available from Chicopee Corporation, New Brunswick, N.J.; Duralace® 1236, an apertured, hydro-entangled material, containing about 100% rayon, and having a basis weight from about 40 gsy to about 115 gsy, available from Chicopee Corporation, New Brunswick, N.J.; Duralace® 5904, an apertured, hydro-entangled material, containing about 100% polyester, and having a basis weight from about 40 gsy to about 115 gsy, available from Chicopee Corporation, New Brunswick, N.J.; Sontaro® 8868, a hydro-entangled material, containing about 50% cellulose and about 50% polyester, and having a basis weight of about 60 gsy, available from Dupont Chemical Corp.

Most preferred as a substrate for purposes of this invention are non-woven substrates, especially blends of rayon/polyester and ratios of 10:90 to 90:10, preferably ratios of 20:80 to 80:20, optimally 40:60 to 60:40 by weight. A most useful substrate is a 70:30 rayon/polyester non-woven substrate.

The amount of impregnating composition relative to the substrate may range from about 20:1 to 1:20, preferably from about 10:1 to about 1:10 and optimally from about 2:1 to about 1:2 by weight.

Foamable compositions of the present invention may also include silicones of a volatile and non-volatile variety. Typical volatile silicones are the cyclomethicones commercially available as Dow Corning 244, 245, 344 and 345. Linear volatile dimethicones are also suitable. Non-volatile silicones include polydimethyl siloxanes of a viscosity greater than 2 centistoke and silicone copolyols also known as dimethicone copolyol for which Dow Corning 193 is a commercial source. Amounts of the silicones may range from about 0.01 to about 20, preferably from about 0.5 to about 3% by weight of the foamable composition.

Cationic conditioning agents of monomeric and polymeric type are also useful for purposes of this invention. Examples of the polymeric type include: cationic cellulose derivatives, cationic starches, copolymers of a diallyl quaternary ammonium salt and an acrylamide, quaternized vinylpyrrolidone, vinylimidazole polymers, polyglycol amine condensates, quaternized collagen polypeptide, polyethylene imine, cationized silicon polymer (e.g. Amodimethicone), cationic silicon polymers provided in a mixture with other components under the trademark Dow Corning 929 (cationized emulsion), copolymers of adipic acid and dimethylaminohydroxypropyl diethylenetriamine, cationic chitin derivatives, cationized guar gum (e.g. Jaguar C-B-S, Jaguar C-17, Jaguar C-16 etc. manufactured by the Celanese Company), quaternary ammonium salt polymers (e.g. Mirapol A-15, Mirapol AD-1, Mirapol AZ-1, etc., manufactured by the Miranol Division of the Rhone Poulenc Company). Most preferred is polyquaternium-11 available as Luviquat® PQ 11 sold by the BASF Corporation.

Examples of monomeric cationic conditioning agents are salts of the general structure:

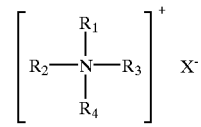

wherein $R^1$ is selected from an alkyl group having from 12 to 22 carbon atoms, or aromatic, aryl or alkaryl groups having from 12 to 22 carbon atoms; $R^2$, $R^3$, and $R^4$ are independently selected from hydrogen, an alkyl group having from 1 to 22 carbon atoms, or aromatic, aryl or alkaryl groups having from 12 to 22 carbon atoms; and $X^-$ is an anion selected from chloride, bromide, iodide, acetate, phosphate, nitrate, sulfate, methyl sulfate, ethyl sulfate, tosylate, lactylate, citrate, glycolate, and mixtures thereof. Additionally, the alkyl groups can also contain ether linkages, or hydroxy or amino group substituents (e.g. the alkyl groups can contain polyethylene glycol and polypropylene glycol moieties). Preferably the anion is phosphate, especially preferred is hydroxy ethyl cetyl dimonium phosphate available as Luviquat® Mono CP from the BASF Corporation.

Amino silicones quats may similarly be employed. Most preferred is Silquat AD designated by the CTFA as Silicone Quatemium 8, available from Siltech Inc.

Amounts of each cationic agent may range from about 0.06 to about 5%, preferably from about 0.1 to about 3%, optimally from about 0.3 to about 2.5% by weight of the foamable composition.

When water or moisture is used or present in the manufacturing process, the resulting treated substrate is then dried so that it is substantially free of water. The term "substantially dry" means the amount of water should not exceed 30% but may range from about 1 to about 15%, preferably no higher than about 4% by weight of the total product. The treated substrate can be dried by any means known to those skilled in the art. Non-limiting examples of known drying means include the use of convection ovens, radiant heat sources, microwave ovens, forced air ovens, and heated rollers or cams. Drying also includes air drying without the addition of heat energy, other than that present in the ambient environment. Also, a combination of various drying methods can be used.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated.

What is claimed is:

1. A substantially dry cleansing product comprising:
   (i) a water insoluble substrate defined by juxtaposed first and second major surfaces, the first major surface being formed with a plurality of upwardly projecting moguls spaced apart from one another; and
   (ii) a foamable composition comprising a lathering surfactant wherein more of the composition is deposited on the second major surface than on the first major surface of the substrate.

2. The product according to claim 1 wherein the mogul has a conical or donut shape.

3. The product according to claim 1 wherein the mogul is of a material different from material forming a web of a substrate.

4. The product according to claim 3 wherein the mogul is formed of an elastomeric material.

5. The product according to claim 1 wherein the mogul is donut shaped.

6. The product according to claim 1 wherein the substrate includes apertures of a size ranging from about 0.01 to 3 mm in a largest dimension, the apertures allowing communication between the first and second surfaces.

7. The product according to claim 1 wherein the moguls contain a colorant to distinguish them from other areas of the substrate.

8. The product according to claim 1 wherein from at least 50% up to about 99.9% by weight of the foamable composition is deposited onto the second surface and from less than 50% down to about 0.1% by weight of the foamable composition is deposited onto the first surface.

9. A method for producing a cleansing article which comprises an apertured water-insoluble substrate having first and second major surfaces opposite one another, the first major surface being formed with a plurality of spaced apart moguls, and the article delivering a foamable composition comprising a lathering surfactant, the method comprising:
   feeding the substrate onto a guide roller, the first major surface of the substrate being juxtaposed against a surface of the guide roller;
   applying the foamable composition to the second major surface of the substrate while the first major surface remains juxtaposed against the guide roller; and
   allowing a minor amount of the applied foamable composition to transfer through the apertured substrate from the second to the first major surface.

10. A substantially dry cleansing product comprising:
    (i) a water insoluble substrate defined by juxtaposed first and second major surfaces, the first major surface being formed with a plurality of upwardly projecting moguls spaced apart from one another, the moguls being separated from one another at their center by a distance of about 0.2 to about 4 cm; and
    (ii) a foamable composition comprising a lathering surfactant wherein more of the composition is deposited on the second major surface than on the first major surface of the substrate.

11. The product according to claim 1 wherein the substrate comprises a single layer.

* * * * *